(12) United States Patent
Komine et al.

(10) Patent No.: US 10,470,653 B2
(45) Date of Patent: Nov. 12, 2019

(54) IMAGE PROCESSING APPARATUS, IMAGE PROCESSING METHOD, AND STORAGE MEDIUM THAT GENERATE A MOTION CONTRAST ENFACE IMAGE

(71) Applicant: CANON KABUSHIKI KAISHA, Tokyo (JP)

(72) Inventors: Isao Komine, Sagamihara (JP); Masashi Kotoku, Yokohama (JP); Nobuhiro Tomatsu, Yokohama (JP); Yukio Sakagawa, Tokyo (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 133 days.

(21) Appl. No.: 15/408,867

(22) Filed: Jan. 18, 2017

(65) Prior Publication Data

US 2017/0231484 A1 Aug. 17, 2017

(30) Foreign Application Priority Data

Feb. 12, 2016 (JP) .................................. 2016-025104

(51) Int. Cl.
*A61B 3/00* (2006.01)
*G06T 7/11* (2017.01)
(Continued)

(52) U.S. Cl.
CPC .......... *A61B 3/0025* (2013.01); *A61B 3/0058* (2013.01); *A61B 3/102* (2013.01);
(Continued)

(58) Field of Classification Search
CPC ..... A61B 3/0025; A61B 3/0058; A61B 3/102; A61B 3/1233; G06T 7/215; G06T 7/11; G06T 7/0012; G06K 9/4604
USPC ........................................ 351/205, 206, 246
See application file for complete search history.

(56) References Cited

U.S. PATENT DOCUMENTS 9,247,872 B2  2/2016 Iwase et al.
9,933,246 B2  4/2018 Takeno et al.
(Continued)

FOREIGN PATENT DOCUMENTS

JP  2013-165953 A  8/2013
JP  2015-131107 A  7/2015

OTHER PUBLICATIONS

Fingler, Jeff et al., "Mobility and transverse flow visualization using phase variance contrast with spectral domain optical coherence tomography", Optics Express, Oct. 1, 2007, vol. 15, No. 20, pp. 12636-12653.
(Continued)

*Primary Examiner* — James R Greece
(74) *Attorney, Agent, or Firm* — Venable LLP

(57) ABSTRACT

An image processing apparatus includes a tomographic signal obtaining unit that obtains tomographic signals of light beams, the light beams respectively having a different polarization from each other and being obtained by splitting combined light obtained by combining return light and reference light, the return light being from an object to be inspected that is irradiated with measuring light, and an information obtaining unit that obtains three-dimensional polarization tomographic information, and three-dimensional motion contrast information of the object to be inspected, by commonly using at least one of the obtained tomographic signals. In addition, an extracting unit extracts a specific region of the object to be inspected using the obtained three-dimensional polarization tomographic information, and an image generating unit generates a motion contrast enface image of the extracted specific region using the obtained three-dimensional motion contrast information.

26 Claims, 7 Drawing Sheets

(51) Int. Cl.
  *A61B 3/10* (2006.01)
  *A61B 3/12* (2006.01)
  *G06K 9/46* (2006.01)
  *G06T 7/00* (2017.01)
  *G06T 7/215* (2017.01)
  *G06K 9/00* (2006.01)

(52) U.S. Cl.
  CPC ........ *A61B 3/1233* (2013.01); *G06K 9/00201* (2013.01); *G06K 9/00885* (2013.01); *G06K 9/4604* (2013.01); *G06T 7/0012* (2013.01); *G06T 7/11* (2017.01); *G06T 7/215* (2017.01); *G06T 2207/10028* (2013.01); *G06T 2207/10101* (2013.01); *G06T 2207/30041* (2013.01); *G06T 2207/30104* (2013.01)

(56) References Cited

U.S. PATENT DOCUMENTS

| | | |
|---|---|---|
| 9,993,152 B2 | 6/2018 | Iwase et al. |
| 2013/0188135 A1 | 7/2013 | Iwase et al. |
| 2014/0221827 A1* | 8/2014 | Motaghiannezam ....................... G01N 21/4795 600/425 |
| 2014/0276025 A1* | 9/2014 | Durbin ................. A61B 5/4842 600/427 |
| 2015/0168127 A1* | 6/2015 | Takeno .............. G01B 9/02091 356/479 |
| 2015/0366448 A1 | 12/2015 | Iwase et al. |
| 2018/0172426 A1 | 6/2018 | Takeno et al. |

OTHER PUBLICATIONS

Zottter, Stefan et al.,"Measuring Retinal Nerve Fiber Layer Birefringence, Retardation, and Thickness Using Wide-Field, High-Speef Polarization Sensitive Spectral Domain OCT", IOVS, Jan. 2013, vol. 54, No. 1, pp. 72-84.

Copending, unpublished U.S. Appl. No. 15/441,884, dated Feb. 24, 2017.

* cited by examiner

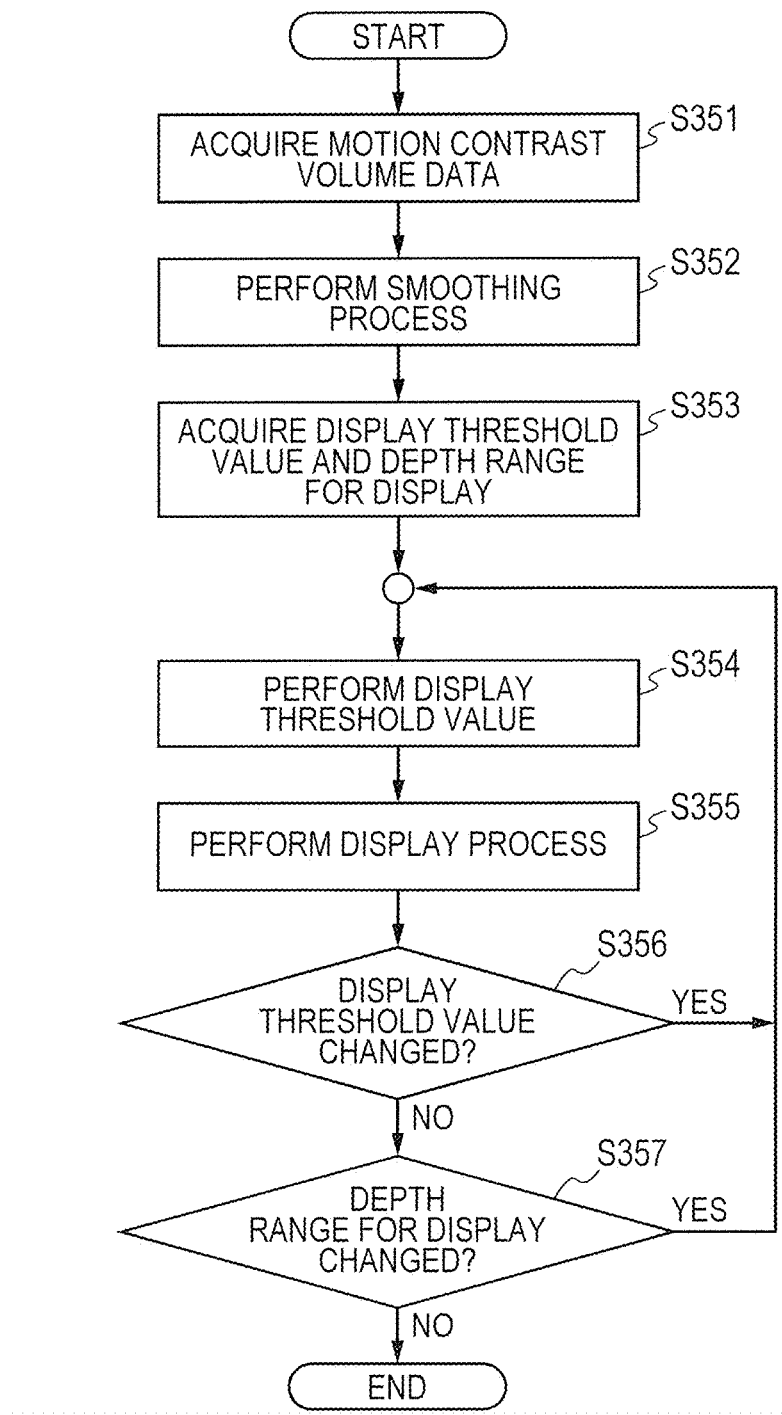

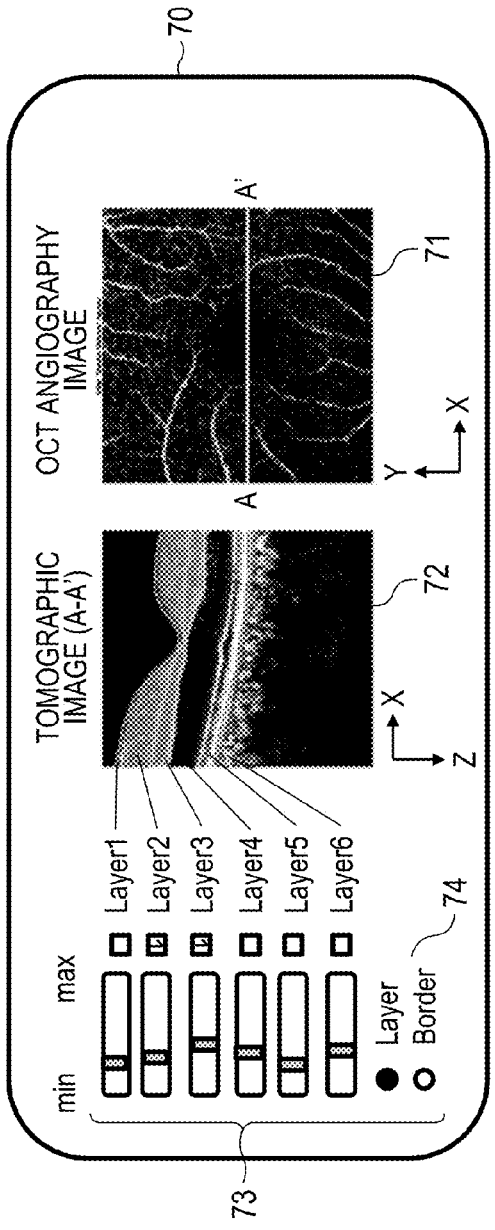
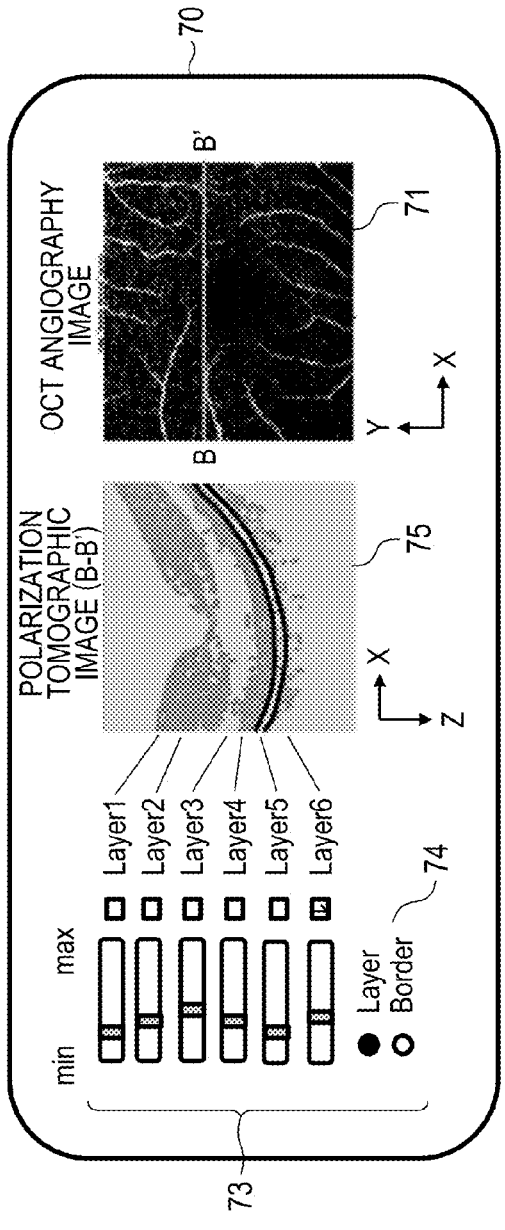
FIG. 8A
FIG. 8B

IMAGE PROCESSING APPARATUS, IMAGE PROCESSING METHOD, AND STORAGE MEDIUM THAT GENERATE A MOTION CONTRAST ENFACE IMAGE

This application claims the benefit of Japanese Patent Application No. 2016-025104, filed Feb. 12, 2016, which is incorporated by reference herein in its entirety.

BACKGROUND OF THE INVENTION

Field of the Invention

The present invention relates to an image processing apparatus, an image processing method, and a storage medium that generate a motion contrast enface image.

Description of the Related Art

As a method of acquiring a tomographic image of an object to be measured, e.g., a living body, in a non-destructive and non-invasive manner, optical coherence tomography (hereafter referred to as "OCT") has been put into practical use. With OCT, particularly in the field of ophthalmology, a tomographic image of a retina in a fundus of an eye to be inspected is acquired, and hence, OCT is widely used for ophthalmologic diagnosis of the retina, or the like.

In OCT, light reflected from the object to be measured and light reflected from a reference mirror are caused to interfere with each other, and time dependence or wavenumber dependence of an intensity of the interference light is analyzed, to thereby acquire a tomographic image. As an optical coherence tomographic image acquisition apparatus applied to such OCT, there are known a time domain OCT apparatus, a spectral domain OCT (SD-OCT) apparatus, and a swept source optical coherence tomography (SS-OCT) apparatus. The time domain OCT apparatus is configured to acquire depth information on the object to be measured by changing a position of the reference mirror. Further, the SD-OCT apparatus uses a broadband light source. The SS-OCT apparatus uses, as a light source, a wavelength-tunable light source apparatus capable of changing an oscillation wavelength. The SD-OCT apparatus and the SS-OCT apparatus are collectively referred to as "Fourier domain optical coherence tomography (FD-OCT)" apparatus.

In recent years, there has been proposed a vessel extraction method using FD-OCT, which is referred to as "OCT angiography (OCTA)". In fluorescence angiography, which is a general vessel extraction method in contemporary clinical medicine, injection of a fluorescent dye (e.g., fluorescein or indocyanine green) into a body is required. Further, a region, through which the fluorescent dye passes, is imaged, to thereby display a vessel two-dimensionally. Meanwhile, OCTA enables non-invasive vessel extraction without injecting a foreign matter into the body, and enables three-dimensional display of a network of the blood flow region. Further, OCTA is attracting attention because OCTA is higher in resolution than fluorescence angiography, and can visualize minute vessels or blood flow of the fundus.

As one of methods of detecting a blood flow in OCTA, in "Mobility and transverse flow visualization using phase variance contrast with spectral domain optical coherence tomography," by Fingler et al., and published in Optics Express. Vol. 15, No. 20. pp. 12636 to 12653 (2007) (Fingler et al.), there is proposed a method of extracting only signals that are changing in time from OCT signals, to thereby separate the OCT signals caused by the blood flow. An image, or the like, generated based on pixels that output signals that are changing in time, which are extracted from the OCT signals, is referred to as a motion contrast image. Further, as another blood flow detecting method, there are also proposed a method utilizing intensity fluctuations due to the blood flow (U.S. Patent Application Publication No. 2014/221827), and a method utilizing phase fluctuations due to the blood flow.

Meanwhile, a polarization-sensitive OCT apparatus, which has been developed as one functional OCT apparatus, can visualize structural information of a nerve fiber layer, a retinal layer, or the like. In "Measuring retinal nerve fiber layer birefringence, retardation, and thickness using wide-field, high-speed polarization sensitive spectral domain OCT," by Zotter et al., published in Invest Opthalmology & Visual Science, (Jan. 7, 2013) (Zotter et al.), there is disclosed a technology using the polarization-sensitive OCT apparatus to obtain an enface map for a retinal nerve fiber layer (RNFL), which is obtained by integrating three-dimensional data per unit thickness in a thickness direction regarding a polarization parameter called retardation.

SUMMARY OF THE INVENTION

In order to solve the above-mentioned problem, in one aspect, the present invention provides an image processing apparatus including an information acquiring unit configured to acquire three-dimensional polarization tomographic information and three-dimensional motion contrast information of an object to be inspected using tomographic signals of light beams having polarizations different from each other, which are obtained by splitting combined light obtained by combining return light from the object to be inspected irradiated with measuring light and reference light corresponding to the measuring light, an extracting unit configured to extract a specific region of the object to be inspected using the three-dimensional polarization tomographic information, and an image generating unit configured to generate a motion contrast enface image of the extracted specific region using the three-dimensional motion contrast information.

Further features of the present invention will become apparent from the following description of exemplary embodiments with reference to the attached drawings.

BRIEF DESCRIPTION OF THE DRAWINGS

FIG. 5 is a flow chart for illustrating an example of a three-dimensional blood flow region information acquiring procedure according to the embodiment.

FIG. 8A is a diagram for illustrating an example of a graphical user interface (GUI) according to the embodiment.

FIG. 8B is a diagram for illustrating an example of the GUI according to the embodiment.

DESCRIPTION OF THE EMBODIMENTS

Figure 1:
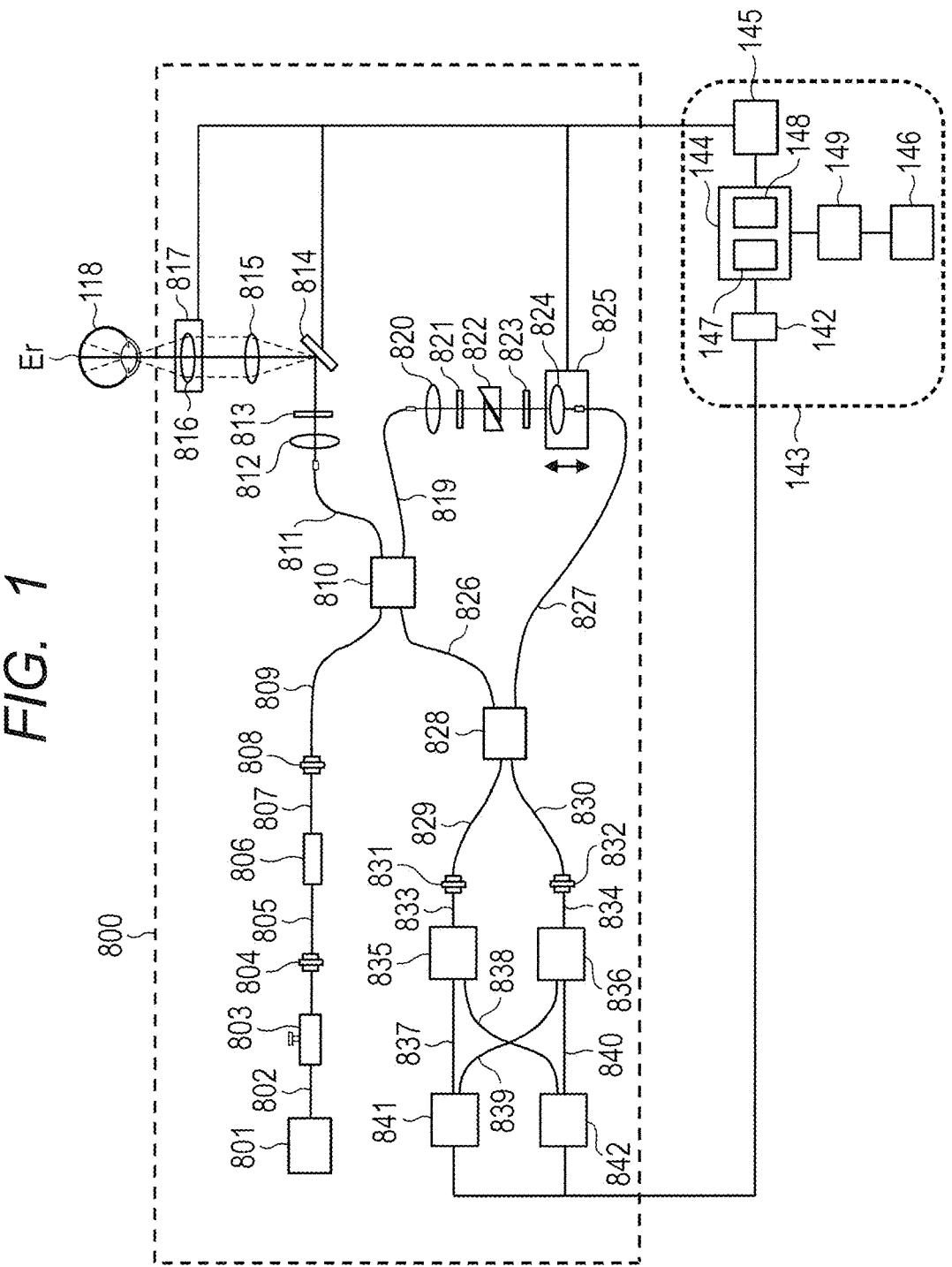
FIG. 1 is a diagram for illustrating an overview of an example of an entire configuration of an apparatus according to an embodiment of the present invention.

When vessel extraction is performed by OCTA, the density of vessels differs for each layer of a retina in a thickness direction. Therefore, in order to perform accurate vessel extraction by a noise process, and the like, it is preferred to specify a retinal layer to be subjected to this extraction process. In this case, the layer in the retina is recognized by a general OCT using luminance information of each layer obtained based on the depth direction.

In layer recognition of a diseased eye, however, when there is a defect, or the like, in the layer structure, the accuracy of the layer recognition may be degraded, and a motion contrast image useful for diagnosis may be unavailable.

In view of the above, it is one object of an embodiment of the present invention to generate a motion contrast image useful for diagnosis even in an eye to be inspected having a disease.

Now, with reference to the accompanying drawings, an image processing apparatus according to this embodiment is described. Configurations described in the following embodiments are merely an example, and the present invention is not limited to the following embodiments. In the embodiments, an object to be inspected is a human eye (fundus), but the present invention is not limited thereto. For example, the object to be inspected may be an organ inside a human body, skin, or the like. Further, in the embodiments, an object to be imaged is the fundus of the eye, but a region other than the fundus, e.g., an anterior segment of the eye may be the object to be imaged.

Polarization-sensitive OCT described in the embodiments, which is one functional OCT, forms an image of the fundus in the depth direction using a polarization parameter, which is one optical characteristic of a fundus tissue. The polarization parameter herein refers to an optical characteristic of the object to be inspected that can be acquired using light beams having respective polarizations (P polarization and S polarization). Examples of the polarization parameter include, in the object to be inspected, retardation (phase delay amount), birefringence, a degree of polarization uniformity (DOPU), and orientation of light beams having respective polarizations.

First Embodiment

In a first embodiment of the present invention, there is described a process of determining, using a layer recognition result obtained based on a polarization information image, a depth range for generating an enface image based on three-dimensional blood flow region information obtained by calculating motion contrast, to thereby generate an image. In this embodiment, a DOPU image, which is one of images generated using polarization information, is used to detect a retinal pigment epithelium (RPE), which is a layer in the retina. The detected RPE is positionally aligned and is then projected with respect to a luminance averaged image of a retina cross section obtained by OCT, to thereby perform segmentation of the RPE in the luminance averaged image. After that, three-dimensional motion contrast data of the layer in the retina specified by the result of the segmentation is integrated in the depth direction by the set range, to thereby generate a motion contrast enface image. Now, details of this configuration are described.

Configuration of OCT Apparatus

First, the configuration of the polarization-sensitive OCT apparatus, which is used for acquiring the three-dimensional luminance information, the three-dimensional blood flow region information, and the polarization information from the eye to be inspected in this embodiment, is described. FIG. 1 is a diagram for illustrating a configuration example of an image processing apparatus configured to perform an image process using the information obtained by the polarization-sensitive OCT apparatus configured to generate each type of information described above. In the embodiment described below, a polarization-sensitive OCT apparatus applying SS-OCT is also described. The present invention is also applicable to a polarization-sensitive OCT apparatus using SD-OCT. The OCT apparatus illustrated in FIG. 1 includes an optical coherence tomographic signal generating portion 800 configured to generate an optical coherence tomographic signal (interference signal), and a control portion 143 configured to control the optical coherence tomographic signal generating portion 800 and to acquire the interference signal to perform an image process.

Configuration of Optical Coherence Tomographic Signal Generating Portion 800

The configuration of the optical coherence tomographic signal generating portion 800 is described with reference to FIG. 1. As a light source 801, a swept source (hereafter referred to as SS) light source is used. The light source 801 is configured to emit light while sweeping a wavelength of the light with a sweeping central wavelength of 1,050 nm and a sweeping width of 100 nm, for example.

The emitted light passes through a single mode fiber (hereafter referred to as an SM fiber) 802, a polarization controller 803, a connector 804, an SM fiber 805, a polarizer 806, a polarization maintaining fiber (hereafter referred to as a PM fiber) 807, a connector 808, and a PM fiber 809, to thereby be guided to a beam splitter 810. The light guided to the beam splitter 810 is split into measuring light (also referred to as OCT measuring light) and reference light (also referred to as reference light corresponding to OCT measuring light). The split ratio of the beam splitter 810 is 90 (reference light):10 (measuring light). The polarization controller 803 can change the polarization of the light emitted from the light source 801 into a desired polarization state.

The polarizer 806 is an optical element having a characteristic of passing only specific linear polarization components. In general, the light emitted from the light source 801 has a high degree of polarization, and light having a specific polarization direction is dominant, but the light emitted from the light source 801 includes light not having a specific polarization direction called a random polarization component. The random polarization component is known to degrade the image quality of the polarization-sensitive OCT image, and, hence, the polarizer 806 is configured to cut the random polarization component. The polarizer 806 can pass only light in a specific linear polarization state, and, hence, the polarization controller 803 adjusts the polarization state such that a desired amount of light enters an eye to be inspected 118.

The measuring light obtained through splitting by the beam splitter 810 is output to a measurement arm via a PM fiber 811, and is converted into collimated light by a collimator 812. The measuring light converted into the collimated light passes through a quarter-wave plate 813, and then enters the eye to be inspected 118 via a galvano scanner 814, a scan lens 815, and a focus lens 816. The galvano scanner 814 is configured to scan the measuring light onto a fundus Er of the eye to be inspected 118. In FIG. 1, the galvano scanner 814 is illustrated as a single mirror, but the galvano scanner 814 actually includes two galvano scanners so as to raster-scan the fundus Er of the eye to be inspected 118.

Further, the focus lens 816 is fixed on a stage 817, and is configured to move in an optical axis direction to adjust the focus of the measuring light on the fundus Er. The galvano scanner 814 and the stage 817 are controlled by a signal acquisition control portion 145 to be described later so that the measuring light can be scanned in a desired range of the fundus Er of the eye to be inspected 118 (also referred to as an acquiring range of a tomographic image, an acquiring position of a tomographic image, and a radiating position of measuring light). The quarter-wave plate 813 is an optical element having a characteristic of delaying a phase between an optical axis of the quarter-wave plate and an axis orthogonal to the optical axis by ¼ wavelength. In this embodiment, the optical axis of the quarter-wave plate is rotated about the optical axis being the rotary axis by 45° with respect to the direction of the linear polarization of the measuring light exiting from the PM fiber 811. In this manner, the light entering the eye to be inspected 118 becomes circularly polarized light.

Although not described in detail in this embodiment, it is desired that the OCT apparatus be provided with a tracking function of detecting movement of the fundus Er to cause the mirrors of the galvano scanner 814 to scan the light while following the movement of the fundus Er. A general technology can be used to perform the tracking function, and the tracking function may be operated in real time, or may be operated in a post process. As a method of performing tracking, there is given, for example, a method using a scanning laser ophthalmoscope (SLO). In this method, a two-dimensional image of the fundus Er within a plane perpendicular to an optical axis is acquired over time using SLO to extract a characteristic portion within the image, e.g., a portion in which a vessel branches. How the extracted characteristic portion within the two-dimensional image has moved is then calculated as a moving amount of the fundus Er, and the calculated moving amount is fed back to the galvano scanner 814. In this manner, real-time tracking can be performed.

As described above, the measuring light is focused on the fundus Er of the eye to be inspected 118 by the focus lens 816 fixed on the stage 817. The measuring light irradiating the fundus Er is reflected or scattered at each layer of the retina, and travels the above-mentioned optical path backward to return to the beam splitter 810. The return light of the measuring light entering the beam splitter 810 passes through a PM fiber 826 to enter a beam splitter 828.

Meanwhile, the reference light obtained through splitting by the beam splitter 810 is output to a reference arm via a PM fiber 819, and is converted into collimated light by a collimator 820. The reference light converted into the collimated light passes through a half-wave plate 821, a dispersion compensation glass 822, an ND filter 823, and a collimator 824 to enter a PM fiber 827. The collimator 824 and one end of the PM fiber 827 are fixed on a coherence gate stage 825. The coherence gate stage 825 is controlled by the signal acquisition control portion 145 so as to be driven in an optical axis direction indicated by the arrow in FIG. 1 depending on the difference in axial length among subjects to be examined. The half-wave plate 821 is an optical element having a characteristic of delaying a phase between an optical axis of the half-wave plate and an axis orthogonal to the optical axis by ½ wavelength. In this embodiment, the linear polarization of the reference light exiting from the PM fiber 819 is adjusted into a polarization state in which the long axis is inclined by 45° in the PM fiber 827. In this embodiment, an optical path length of the reference light is changed to obtain a condition for causing interference light. The configuration for generating the interference light is not, however, limited thereto, and it is only required that an optical path length difference between the optical path of the measuring light and the optical path of the reference light may be changed. The reference light passing through the PM fiber 827 enters the beam splitter 828.

In the beam splitter 828, the return light of the measuring light and the reference light are combined to obtain combined light, that is, interference light, and, then, the obtained light is split into two beams. The split interference light beams are interference light beams having phases inverted to each other (hereafter expressed as a positive component and a negative component). The positive component of the split interference light passes through a PM fiber 829, a connector 831, and a PM fiber 833 to enter a polarization beam splitter 835. Meanwhile, the negative component of the interference light passes through a PM fiber 830, a connector 832, and a PM fiber 834 to enter a polarization beam splitter 836.

In each of the polarization beam splitters 835 and 836, in conformity with the two orthogonal polarization axes, the entering interference light is split into two light beams, specifically, light having a vertical polarization component (hereafter referred to as a V polarization component) and light having a horizontal polarization component (hereafter referred to as an H polarization component). That is, the positive interference light entering the polarization beam splitter 835 is split by the polarization beam splitter 835 into two interference light beams, specifically, light having a positive V polarization component and light having a positive H polarization component. The split light having the positive V polarization component passes through a PM fiber 837 to enter a detector 841, and the split light having the positive H polarization component passes through a PM fiber 838 to enter a detector 842. Meanwhile, the negative interference light entering the polarization beam splitter 836 is split by the polarization beam splitter 836 into light having a negative V polarization component and light having a negative H polarization component. The light having the negative V polarization component passes through a PM fiber 839 to enter the detector 841, and the light having the negative H polarization component passes through a PM fiber 840 to enter the detector 842.

Both of the detectors 841 and 842 are differential detectors in which, when two interference signals having phases inverted to each other by 180° are input, a DC component is removed, and only an interference component is output. A tomographic signal $A_V$ of the vertical polarization (V polarization) component detected by the detector 841 and a tomographic signal $A_H$ of a horizontal polarization (H polarization) component detected by the detector 842 are output as electrical signals corresponding to the intensity of the light. The output electrical signals are input to a signal processing portion 144 to be described later, which is an example of a tomographic image generating portion.

Configuration of Control Portion 143

Next, a description is given of the configuration and the function of the control portion 143 configured to control the entire polarization-sensitive OCT apparatus and to use the interference signal acquired by the polarization-sensitive OCT apparatus to perform various types of processes as the image processing apparatus. The control portion 143 includes a signal acquiring portion 142, the signal processing portion 144, the signal acquisition control portion 145, a display portion 146, and a display control portion 149. Further, the signal processing portion 144 further includes an image generating portion 147 and a map generating portion 148. The signal acquiring portion 142 is configured to acquire electrical signals (interference signals) transmitted from the detectors 841 and 842 to output those signals to the signal processing portion 144. The image generating portion 147 serving as an image generating unit is configured to convert a wavelength of an interference signal into a wave number to perform Fourier transform, to thereby generate a tomographic signal including information relating to a cross section of the object to be inspected (also referred to as a tomographic signal representing a polarization state). Further, the image generating portion 147 has a function of generating a polarization characteristic image from the interference signal transmitted to the signal processing portion 144. Still further, the image generating portion 147 has a function of generating a luminance image (luminance tomographic image) and a motion contrast image (motion contrast tomographic image), to be described later, from the information obtained by the interference signal. Further, the map generating portion 148 has a function of generating layer information (retina segmentation) from a luminance averaged image, to be described later. The map generating portion 148 further has a function of detecting the nerve fiber bundle and the retinal pigment epithelium using data for generating the polarization characteristic image.

In more detail, the signal processing portion 144 is configured to generate data to be used by the image generating portion 147 for image generation, to analyze the generated image, and to generate visible information of the analysis result based on the signals output from the detectors 841 and 842. The data, analysis result, and visible information generated by the signal processing portion 144 are sent to the display control portion 149, and the display control portion 149, serving as a display control unit, displays the data, analysis result, and visible information as appropriate on a display screen of the display portion 146, serving as a display unit. The display portion 146 is a display, e.g., a liquid crystal display. Image data generated by the signal processing portion 144 may be transmitted to the display portion 146 in a wired or wireless manner after being sent to the display control portion 149. Further, although the display portion 146 and other portions are included in the control portion 143 in this embodiment, the present invention is not limited thereto. The display portion 146 and other portions may be provided separately from the control portion 143, and may be, for example, a tablet computer, which is an example of a device that can be carried around by a user.

In this embodiment, the signal acquiring portion 142 is configured to acquire the interference signal (tomographic signal) generated by the optical coherence tomographic signal generating portion 800, and the control portion 143 is configured to use the acquired tomographic signal to execute each type of process to be described later. The mode of the image processing apparatus according to the present invention is not, however, limited thereto, and the signal acquiring portion 142 may acquire a tomographic signal that is acquired by the optical coherence tomographic signal generating portion 800 in advance and stored in a memory (not shown) or in an external storage device, and this acquired tomographic signal may be used to perform the process. That is, the image processing apparatus exemplified in the form of the control portion 143 is only required to be connected to the optical coherence tomographic signal generating portion 800 being the OCT apparatus so that communication is possible therebetween.

Scan Pattern

Measuring light scanning of radiating the measuring light to the eye to be inspected 118 to acquire information relating to the cross section of the eye to be inspected 118 in its depth direction is referred to as an A-scan, and the depth direction is referred to as an A-scan direction. Further, measuring light scanning for acquiring information relating to a cross section in one direction in the scanning direction of the eye to be inspected 118, which is a direction orthogonal to the A-scan direction, that is, measuring light scanning for acquiring a two-dimensional image in a plane including the one direction and the depth direction, is referred to as a B-scan. Further, the one direction in which the measuring light is scanned in this case is referred to as a B-scan direction. Further, measuring light scanning in a direction orthogonal to both scanning directions of the A-scan direction and the B-scan direction (orthogonal to the plane for obtaining the two-dimensional image) is referred to as a C-scan. The scanning direction for the C-scan is referred to as a C-scan direction.

In this case, in the OCT apparatus, when the measuring light is two-dimensionally raster-scanned on the fundus in order to acquire a three-dimensional tomographic image of the fundus, high-speed scanning is performed in the B-scan direction. Further, low-speed scanning is performed in the C-scan direction in order to scan the measuring light such that the scanning lines of the B-scan are aligned in a direction orthogonal to the B-scan direction. A two-dimensional tomographic image can be obtained by performing the A-scan and the B-scan, and a three-dimensional tomographic image can be obtained by performing the A-scan, the B-scan, and the C-scan. The measuring light is scanned in the B-scan and the C-scan by the above-mentioned galvano scanner 814.

Next, an example of a scan pattern of the measuring light of this embodiment is described with reference to FIG. 2.

In OCTA, in order to measure the change with time of the OCT interference signal due to the blood flow, measurement is required to be performed a plurality of times at the same position (or substantially the same position). In this embodiment, the OCT apparatus performs scanning of repeating the B-scan at the same position m times, and, then, moves the scanning position of the measuring light to n y-positions. A specific scan pattern is illustrated in FIG. 2. At each of the n y-positions of y1 to yn on the fundus plane, the B-scan is repeated m times.

In order to correctly measure the change with time of the interference signal, those m times of B-scan are required to be performed at the same position on the fundus. The eye to be inspected always performs involuntary eye movement during fixation, however, and, hence, the measuring light scanning at the same position is actually not easy even when scanning is intended on the same scanning line. The measuring light scanning that is performed with the intention to B-scan the measuring light on the same-position scanning line is herein referred to as scanning the measuring light on the same scanning line, or acquiring the interference signal of the same cross section. Further, it is conceivable to execute B-scan a plurality of times while slightly shifting the scanning line intentionally, and to perform averaging or other processes on the obtained interference signals regarding pixels corresponding thereto, to thereby reduce noise. In this case, those substantially equal scanning lines of the measuring light are expressed as the same scanning line, and, further, the tomographic image obtained through the averaging or other processes is also expressed as the tomographic image obtained from the same scanning line.

In this case, as the value of m, which is the number of repetition times, becomes larger, the number of measurement times at the same position also increases, and, hence, an accuracy of detecting the blood flow increases. Meanwhile, the scan time increases, and, hence, there arise fears that a motion artifact occurs in an image due to movement of an eye (involuntary eye movement during fixation) during a scan and that burden on the subject to be examined increases. In this embodiment, m is determined in consideration of the balance between the detection accuracy and the measurement time. The control portion 143 may change m depending on an A-scan speed of the OCT apparatus and motion analysis of a fundus surface image of the eye to be inspected 118.

Figure 2:
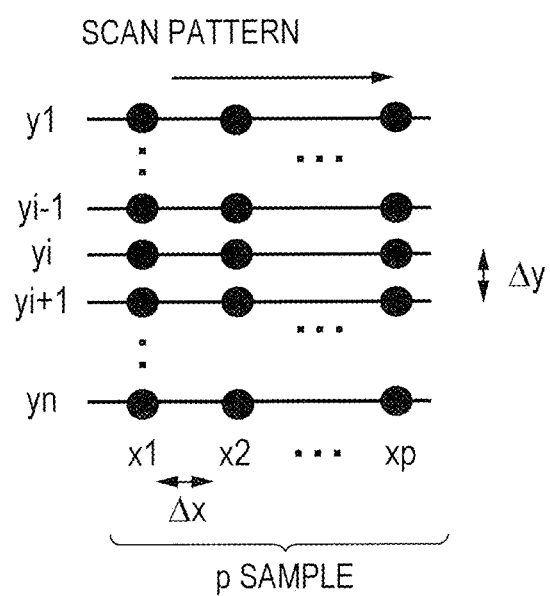
FIG. 2 is an explanatory diagram for illustrating an example of a scan pattern of measuring light according to the embodiment.

In FIG. 2, p represents the number of samples of the A-scan in one B-scan. In other words, the size of the plane image is determined based on p×n. As p×n becomes larger, a wider range can be scanned as long as a measurement pitch is the same. The scan time increases, however, and, hence, the above-mentioned motion artifact and increase in the burden on the subject to be examined are required to be taken into consideration. Therefore, n and p can be freely changed as appropriate depending on those requirements. Further, Δx of FIG. 2 is an interval (x-pitch) between x-positions that are adjacent A-scan positions, and Δy of FIG. 2 is an interval (y-pitch) between y-positions that are adjacent B-scan positions.

Interference Signal Process Flow until Motion Contrast Data Acquisition

A flow of an image processing method executed until acquisition of the motion contrast data, which is a process of the interference signal in this embodiment, is described with reference to FIG. 3. In Step S210 of FIG. 3, the signal processing portion 144 sets an index i of a position yi to 1. In Step S220, the signal processing portion 144 extracts a plurality of data sets including interference signals for m times of measurement, which are obtained by repeated B-scans at the position yi. In Step S230, the signal processing portion 144 sets an index j of the repeated B-scans to 1. In Step S240, the signal processing portion 144 extracts a data set obtained by the B-scan at a Jth line of the interference signals obtained by the repeated B-scans. The image generating portion 147 subjects the interference signals extracted as the data set to a reconstruction process, to thereby generate a luminance image (two-dimensional luminance image in the depth direction).

Now, the interference signal process performed by the image generating portion 147 is described. The image generating portion 147 can perform the reconstruction process on the interference signals obtained from respective light beams having the H polarization component and the V polarization component, which are respectively output from the detectors 841 and 842. First, the image generating portion 147 removes fixed pattern noise from the interference signal. The fixed pattern noise is removed by averaging the plurality of detected A-scan signals to extract the fixed pattern noise, and subtracting the fixed pattern noise from the input interference signal.

Next, the image generating portion 147 performs a desired window function process in order to optimize the depth resolution and the dynamic range that have a trade-off relationship when Fourier transform is performed at a finite interval. After that, the image generating portion 147 subjects each of the interference signals obtained from the light having the H polarization component and the light having the V polarization component to a Fast Fourier Transform (FFT) process to generate the luminance image. The luminance image based on each polarization component obtained by the polarization-sensitive OCT is basically the same as the luminance image obtained in the related-art OCT. A pixel value r for generating the luminance image is calculated by Expression 1 based on the tomographic signal (interference signal) $A_H$ of the H polarization component and the tomographic signal (interference signal) $A_V$ of the V polarization component, which are obtained by the detectors 841 and 842.

$$r=\sqrt{A_H^2+A_V^2}$$ Expression 1.

Next, in Step S250, the image generating portion 147 increments the index j of the repeated B-scans. In Step S260, the image generating portion 147 determines whether or not the index j is greater than the number m of repetition times. That is, the image generating portion 147 determines whether or not the luminance calculation for the B-scan data at the position yi is repeated for m times. When the determination result is No, the flow returns to Step S240, and the luminance calculation of the data set for the next B-scan in the data sets of the repeated B-scans at the same y-position is repeated. That is, the image generating portion 147 acquires a plurality of pieces of luminance image data (tomographic images) representing the cross section at substantially the same location of the eye to be inspected 118. Those pieces of data construct part of three-dimensional luminance tomographic information, to be described later.

On the other hand, when Yes is determined in Step S260, the flow proceeds to Step S270. In Step S270, the image generating portion 147 performs position alignment of m frames that are a plurality of data sets of the repeated B-scans at a certain position yi. Specifically, first, the image generating portion 147 selects one arbitrary frame from the m frames as a template. The frame to be selected as a template may be selected by calculating correlations in all of the combinations, obtaining the sum of correlation coefficients for each frame, and selecting the frame having the maximum sum. Next, the image generating portion 147 obtains misalignment amounts (δX, δY, and δθ) by comparing the template with each frame. Specifically, the image generating portion 147 calculates a normalized cross-correlation (NCC) that is an index representing the similarity while changing the position and the angle of the template image, and obtains the difference of the image position when the value of NCC is the maximum as the misalignment amounts.

Next, the image generating portion 147 applies position correction to the (m−1) frames other than the template in accordance with the misalignment amounts (δX, δY, and δθ), to thereby perform position alignment of the m frames. After the position alignment of each of the data sets is ended, in Step S280, the image generating portion 147 generates luminance images of the m frames based on each of the data sets. After the luminance image generation, in Step S290, the image generating portion 147 averages the plurality of luminance images subjected to position alignment, which are obtained in Step S270 and Step S280, to thereby generate a luminance averaged image.

Segmentation in Luminance Averaged Image

Figure 7:
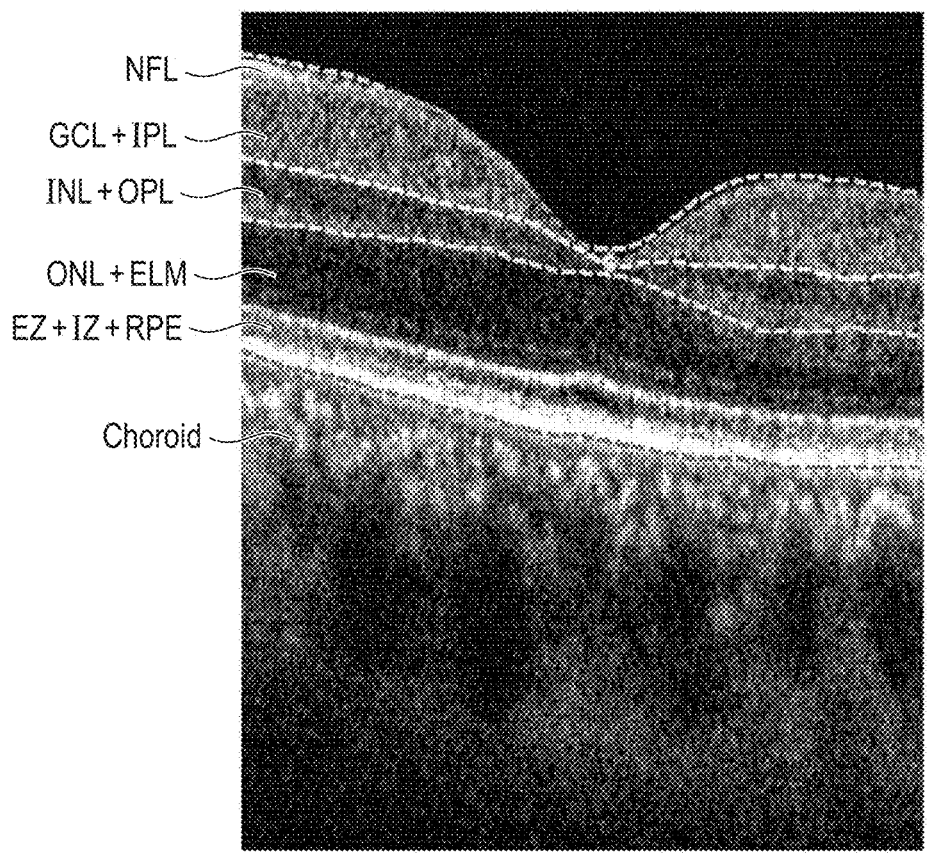
FIG. 7 is an image for showing an example of a segmentation result according to the embodiment.

In Step S300, the map generating portion 148 performs segmentation (region information acquisition) of the retina from the luminance averaged image generated by the image generating portion 147 in Step S290. The fundus of the eye to be inspected 118 being the object to be imaged is widely known to have the layer structure as shown in FIG. 7. Further, considering that the vessel density differs depending on each retinal layer in the depth direction, it is preferred to set variably a threshold value for detecting the blood flow region for each layer. Step S300 is a step of performing segmentation of this layer structure, and six layers can be detected in this embodiment. That is, the process in Step S300 corresponds to an example of a step of detecting layers from the luminance averaged image data. The number of layers to be detected is not limited to six. In this case, the details of the six layers are (1) a nerve fiber layer (NFL), (2) a combined layer of a ganglion cell layer (GCL) and an inner plexiform layer (IPL), (3) a combined layer of an inner nuclear layer (INL) and an outer plexiform layer (OPL), (4) a combined layer of an outer nuclear layer (ONL) and an external limiting membrane (ELM), (5) a combined layer of an ellipsoid zone (EZ), an interdigitation zone (IZ), and a retinal pigment epithelium (RPE), and (6) a choroid.

The map generating portion 148 generates images by applying each of a median filter and a Sobel filter to a tomographic image that is extracted from the luminance averaged image to be processed (hereafter respectively also referred to as a median image and a Sobel image). Next, profiles are generated for each A-scan from the generated median image and Sobel image. The median image corresponds to the profile of the luminance value, and the Sobel image corresponds to the profile of the gradient. Then, a peak in the profile generated from the Sobel image is detected. With reference to the profile of the median image corresponding to a part before or after the detected peak or a part between the peaks, the border of each region of the retinal layer is extracted.

Generation of DOPU Image and Segmentation using DOPU Image

Meanwhile, from the polarization-sensitive OCT image, that is, from the tomographic signal $A_H$ of the H polarization component and the tomographic signal $A_V$ of the V polarization component obtained from the detectors 841 and 842, the polarization information of the eye to be inspected 118 can be obtained. The image generating portion 147 is configured to generate an averaged DOPU image using the polarization information after the above-mentioned luminance image is generated or in parallel with the generation of the luminance image. The degree of polarization uniformity (DOPU) is a numerical value representing the uniformity of polarization, and is one of the polarization characteristic images obtained by subjecting the polarization characteristic of the eye to be inspected to an image process. The polarization characteristic images include, in addition to this DOPU image based on depolarization information, for example, an image based on retardation information, an image based on orientation information, and an image based on birefringence information. Those images and information construct the three-dimensional polarization tomographic information.

Figure 4:
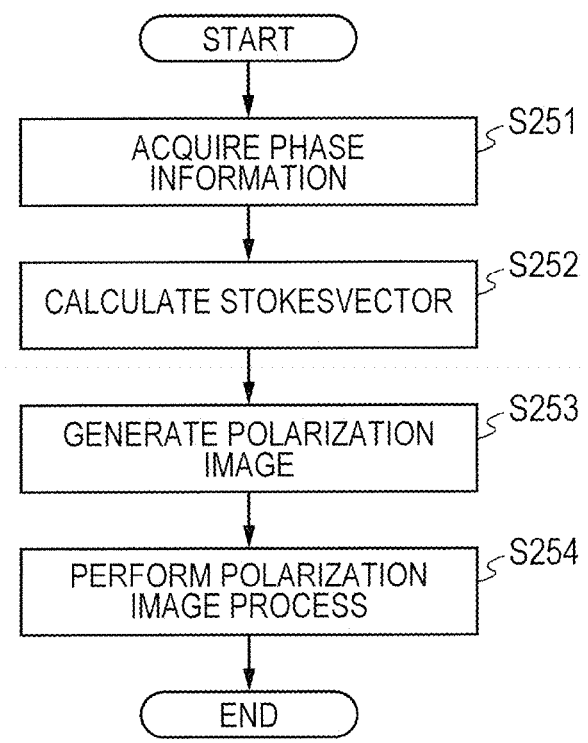
FIG. 4 is a flow chart for illustrating an example of a polarization image processing procedure according to the embodiment.

Now, with reference to FIG. 4, a procedure of generating the DOPU image in this embodiment is described.

In Step S251, the image generating portion 147 acquires the tomographic signals $A_H$ and $A_V$ of the respective polarization components of the m frames and a phase difference $\Delta\Phi$ therebetween. In Step S252, the image generating portion 147 calculates a stokes vector S for each pixel by Expression 2.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix}$$ Expression 2

In this case, $\Delta\Phi$ is calculated as $\Delta\Phi=\Phi_V-\Phi_H$ based on phase differences $\Phi_H$ and $\Phi_V$ of respective signals obtained when two tomographic images are calculated.

Next, in Step S253, the image generating portion 147 sets, for each B-scan image, a window with size of substantially 70 μm in the main scanning direction of the measuring light and about 18 μm in the depth direction. After the setting, respective elements of the stokes vector calculated for each pixel by Expression 2 in each window are averaged, to thereby calculate the uniformity DOPU of the polarization in the window by Expression 3.

$$DPOU=\sqrt{Q_m^2+U_m^2+V_m^2}$$ Expression 3.

In this case, $Q_m$, $U_m$, and $V_m$ are values obtained by averaging elements Q, U, and V of the stokes vector in each window. By calculating the DOPU for all of the windows in the B-scan image, a DOPU image (also referred to as a tomographic image representing the uniformity of the polarization) is generated.

Next, in Step S254, the image generating portion 147 performs a process of imaging the value of the DOPU, to thereby obtain the DOPU image from the polarization information (three-dimensional data). Further, the image generating portion 147 is an example of an extracting unit, and is configured to use the obtained DOPU image to perform segmentation of specifying the retinal pigment epithelium (hereafter referred to as RPE) from the layers in the retina. After the DOPU image is acquired, the flow illustrated in FIG. 4 is ended. The process described here corresponds to, in FIG. 3, a polarization information averaging process by the image generating portion 147 in Step S310 with respect to the polarization image, a DOPU image generation process of Step S320, and polarization segmentation for specifying the RPE in Step S330. The position of the RPE can be obtained based on the DOPU image obtained through the above-mentioned processes or the data for generating the image. In the above-mentioned segmentation using the luminance averaged image, the border of the RPE may be unclear due to the diseased eye, or the like, but the RPE can be accurately detected with the DOPU image. Details of this fact are described below.

The DOPU becomes a numerical value close to 1 at a location where the polarization is maintained, and becomes less than 1 at a location where the polarization is not maintained. In the structure of the retina, the RPE has a property of depolarizing the polarized state, and, hence, the numerical value of the part corresponding to the RPE in the DOPU is less than the values of other regions. The DOPU image obtained by imaging the values of the DOPU is an image of a depolarized layer, e.g., the RPE. Therefore, even when the RPE is deformed due to a disease, or the like, the RPE or a discrete RPE corresponding region due to lesion can be identified more reliably than using the change in luminance. The identification information of the RPE is temporarily stored at this time.

It should be noted that, as is understood from the generation method of the DOPU image, the DOPU image is reduced in resolution as compared to the luminance image, and, hence, the border or the shape of the RPE can be more precisely determined when the luminance image is used. For example, the position of the RPE may be acquired by extracting the RPE from the DOPU image, and the acquired position may be used to extract a high luminance region as the RPE from the luminance image. This method may be performed in place of Step S340 (segmentation adjustment), described later. Further, in this embodiment, a case in which the RPE is identified using the DOPU image is described as an example, but without limitation to the DOPU image or the RPE, it is further effective to identify other layers using other polarization characteristic images. For example, it is preferred to perform identification of the RNFL, identification of the lesion region, or the like, using the image based on the retardation information, the image based on the orientation information, or the image based on the birefringence information.

Segmentation Adjustment

Next, a method of correcting, based on the DOPU image, the region of the RPE in the result obtained by the segmentation of the luminance averaged image is described. In Step S340 of FIG. 3, the image generating portion 147 performs position alignment between the DOPU image and the luminance averaged image, and corrects the RPE region of the luminance averaged image based on the position information of the RPE obtained from the DOPU image. That is, the RPE or the discrete RPE corresponding region due to the lesion identified from the DOPU image is projected onto the luminance averaged image, and the high luminance part in this region is extracted, to thereby determine the extracted region as a final RPE or a region corresponding thereto. Further, the map generating portion 148 performs combination with other retina segmentation results using the above-mentioned luminance averaged image.

Motion Contrast Calculation

Figure 3:
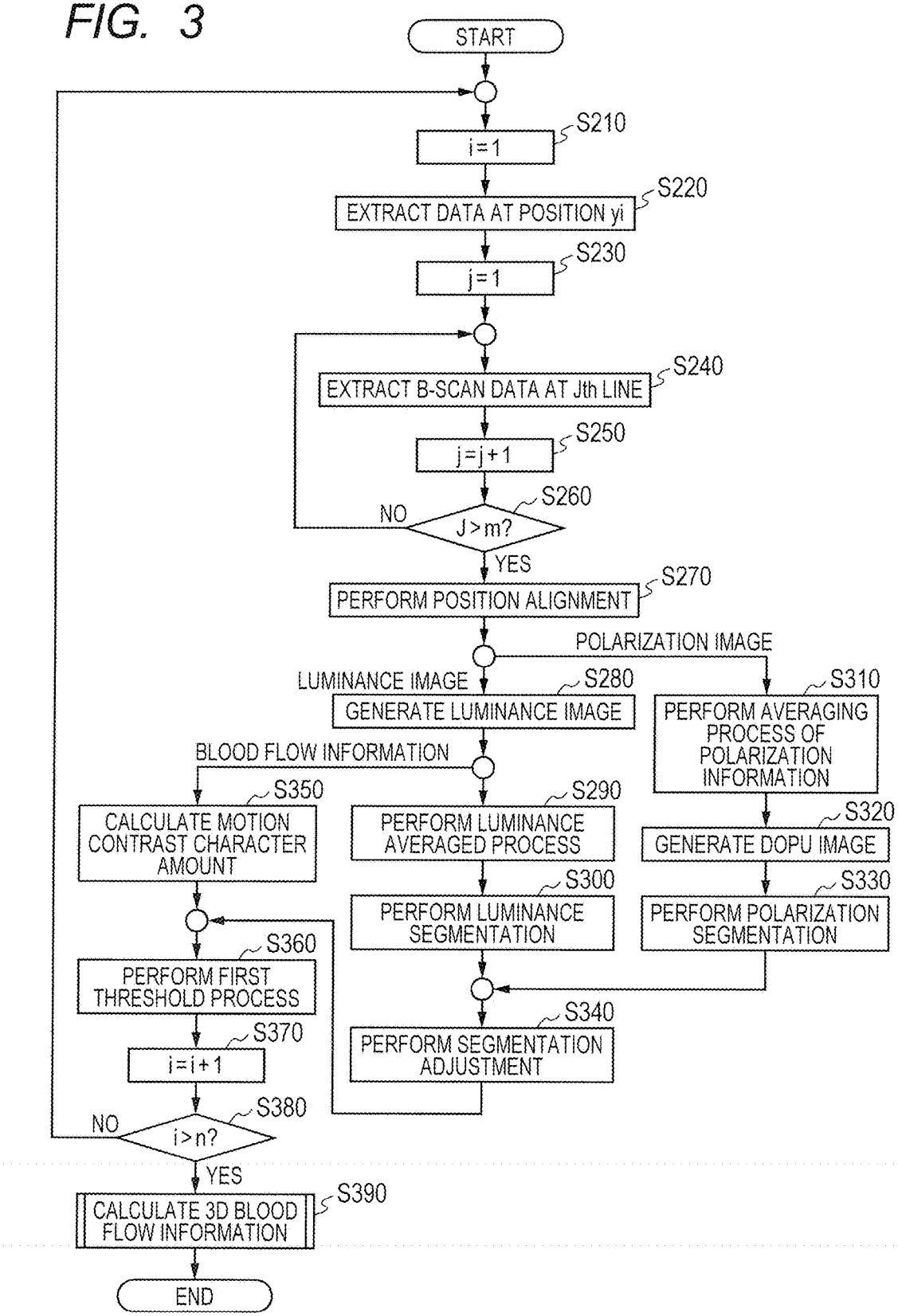
FIG. 3 is a flow chart for illustrating an example of a signal processing procedure according to the embodiment.

In Step S350 of FIG. 3, the image generating portion 147 calculates a motion contrast. The motion contrast is generated using a signal representing time modulation between corresponding pixels among the plurality of tomographic signals obtained by scanning the measuring light that is scanned with the intention to acquire the tomographic signal of the same cross section. In this embodiment, in Step S280, the dispersion value of the signal intensity (luminance) is calculated for each pixel at the same position from the luminance images of the m frames output by the signal processing portion 144, and this dispersion value is set as the motion contrast. That is, the image generating portion 147 calculates the motion contrast using the corresponding pixel data among the data sets of the plurality of calculated luminance images.

Other than the dispersion value, any one of a standard deviation, a difference value, a decorrelation value, and a correlation value may be used. Further, the phase may be used instead of the signal intensity. Further, there are various methods for obtaining the motion contrast. In the present invention, the method is applicable as long as the type of a motion contrast character amount is an index representing the change in luminance value of each pixel of the plurality of B-scan data sets at the same y-position. Further, the motion contrast can use a variation coefficient that is normalized by an average value of each pixel at the same position in each frame, instead of the dispersion value of each pixel at the same position in the luminance images of the m frames. The obtained motion contrast data constructs part of three-dimensional motion contrast information, to be described later.

In Step S360, the signal processing portion 144 performs a first threshold processing on the motion contrast calculated by the image generating portion 147. As a first threshold value, a standard deviation σ and the segmentation information acquired in Step S340 are used. As an example of the threshold processing, in this embodiment, the RPE segmentation information (information representing the RPE) obtained in Step S340 is used to set a noise threshold value of the motion contrast in the RPE. Specifically, it is conceivable to reduce the noise at a deep position by setting the threshold value for the RPE to be greater than the threshold value for a region above the RPE, or setting the threshold value for a region deeper than the RPE to be greater than the threshold values for other regions. As described above, the noise threshold value can be set for each layer specified in accordance with the segmentation information.

Further, the value of the motion contrast can be corrected using the fact that the RPE is a non-vessel region. For example, even when the RPE is divided, the depolarization region has no blood flow, and, hence, the motion contrast value of the detected RPE may be corrected to 0. In this manner, the threshold processing can be more accurately performed in Step S360. With this, the information relating to the blood flow in the tomographic image at the position yi can be extracted.

After the threshold processing is ended, in Step S370, the signal processing portion 144 increments the index i of the position yi. After the increment, in Step S380, the signal processing portion 144 determines whether or not i is greater than n. That is, the signal processing portion 144 determines whether or not the position alignment, the luminance averaged calculation, the motion contrast calculation, and the threshold processing are performed at all of the n y-positions. In the case of No, the flow returns to Step S210. In the case of Yes, the flow proceeds to next Step S390. The polarization image process (S310, S320, and S330), the luminance image process (S280, S290, and S330), and the blood flow information process (S350) are not limited to be performed before Step S370 and Step S380, and may be performed after Step S370 and Step S380.

At a time point at which Step S380 is ended, there are acquired a luminance averaged image and three-dimensional data of the motion contrast of each pixel of a B-scan image (planar image having two axes of the depth direction and an x direction being a measuring light scanning direction) of all of the y-positions. The acquisition of the B-scan image at the plurality of y-positions corresponds to the acquisition of the three-dimensional tomographic image data in the fundus of the eye to be inspected. In Step S390, using the three-dimensional motion contrast data subjected to the threshold processing, which is obtained through the flow described above, calculation of the three-dimensional blood flow information, estimation of the vessel, or other processes is performed. After the process in Step S390 is ended, this flow is ended. The image generating portion 147 temporarily stores the three-dimensional data of the calculated motion contrast in Step S390.

Display Process Flow

The three-dimensional motion contrast data obtained by the above-mentioned signal process is imaged to be displayed on the display portion 146. Next, with reference to FIG. 5, a display process in this embodiment from the imaging to the display is described. In this embodiment, there is a feature in that the display range of the motion contrast image in the depth direction is set through selection of a layer based on the result of the segmentation adjustment performed in Step S340 described above. That is, the display range is selected using the detected layer.

At the time of the display process, in Step S351, the signal processing portion 144 acquires the three-dimensional motion contrast data acquired as described above. In Step S352, in order to remove noise without removing the blood flow region information, the signal processing portion 144 performs a smoothing process on the three-dimensional motion contrast data.

At that time, although the optimal smoothing process differs depending on a characteristic of the motion contrast, the following smoothing methods are conceivable, for example: a method of outputting a maximum value of the motion contrasts from nxxnyxnz voxels near a pixel of interest, a method of outputting an average value of the motion contrasts of those voxels, and a method of outputting a median value of the motion contrasts of those voxels. Further, the following methods are also conceivable: a method of weighting with a weight that is based on a distance with regard to the motion contrasts of the nxxnyxnz voxels near the pixel of interest, and a method of weighting with a weight that is based on the distance and a weight that is based on the difference in pixel value from the pixel of interest with regard to the motion contrasts of those voxels. In other cases, a method of outputting a value using a weight that is based on a similarity between a motion contrast pattern of a small region around the pixel of interest and a motion contrast pattern of a small region around a surrounding pixel is also conceivable. Another method of performing averaging without removing other blood flow region information may also be used.

Next, in Step S353, the signal processing portion 144 obtains a display threshold value for determining the pixel to be displayed and an initial value of the layer to be displayed. As the initial value of the display range, for example, four layers from the surface layer, specifically, the nerve fiber layer (NFL), the ganglion cell layer (GCL), the inner plexiform layer (IPL), and the inner nuclear layer (INL) are set. Further, using the result of the segmentation adjustment obtained in Step S340, for example, a range that is above the RPE by more than 20 μm may be specified, or a range that is above the RPE by from 20 to 30 μm may be specified. That is, a predetermined range in the fundus with a specific layer, e.g., the RPE, or a layer border being a reference can be specified as the display range.

As the initial value, at least three layers may be selected from the four layers from the surface layer. It is desired, however, that successive layers be selected when a plurality of layers are selected as the initial value. Further, when there is a layer that cannot be separated through segmentation of the retinal layer in this case, this layer is desired to be expressed as a combined layer. The initial value of the display range in this case is not set to the entire retinal layer because the main vessels and the capillary network in the surface layer portion are desired to be displayed first in an easy-to-view manner. That is, when the surface layer portion including the main vessels and the capillary network and an RPE layer, which does not have vessels and contains a large amount of noise, are simultaneously displayed, the discrimination between the main vessels and the capillary network in the surface layer portion may be affected.

Figure 6A:
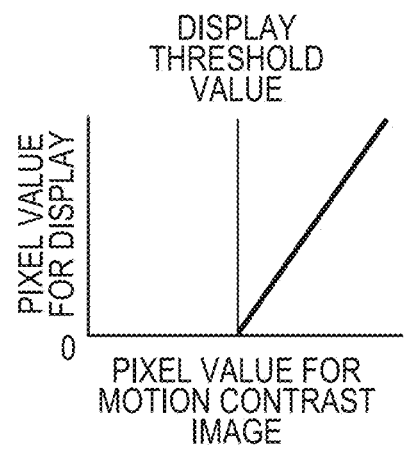
FIG. 6A and FIG. 6B are each a graph for showing an example of a method of converting a pixel value for a motion contrast image into a pixel value for display according to the embodiment.
Figure 6B:
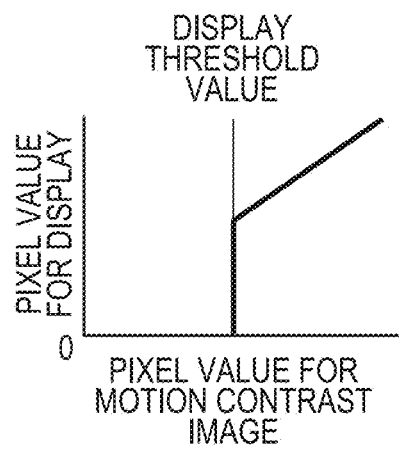

Next, in Step 354, the signal processing portion 144 performs a display threshold process on each pixel of the three-dimensional motion contrast data subjected to the averaging process using the initial value of the display threshold value. Examples of conversion from a pixel value for a motion contrast image into a pixel value for display in this process are shown in FIG. 6A and FIG. 6B. In FIG. 6A, an example is shown in which a pixel value for display of 0 is assigned to a pixel having a pixel value for a motion contrast image equal to or less than the display threshold value and a pixel value for display proportional to a pixel value for a motion contrast image is assigned to a pixel having a pixel value for a motion contrast image greater than the threshold value and equal to or less than the maximum intensity. In FIG. 6B, an example is shown in which a pixel value for display multiplied by 0 is assigned to a pixel value for a motion contrast image equal to or less than the display threshold value and a pixel value for display multiplied by 1 is assigned to a pixel value for a motion contrast image greater than the threshold value.

In any of the cases, in a pixel having a motion contrast that is equal to or less than the display threshold value, its motion contrast is disabled, and the pixel is thereafter treated as a pixel that has no possibility of representing the presence of the blood flow. Therefore, a region having a motion contrast having a connection to be displayed as the vessel is displayed in a form of being separated from the disabled pixel. That is, the motion contrast value is controlled based on the comparison result between the motion contrast and the threshold value. The process in Step S354 described above corresponds to an example of a step of comparing between the motion contrast and the display threshold value and a step of disabling the motion contrast that is equal to or less than the display threshold value using the comparison result.

In Step S355, as illustrated in FIG. 8A, the display control portion 149 performs a display process of displaying the motion contrast image subjected to the display threshold processing on the display portion 146. In the display process, for example, as illustrated in FIG. 8A, a two-dimensional motion contrast enface image 71, a luminance averaged image (two-dimensional luminance tomographic image) 72, and a graphical user interface (GUI) 73 are displayed. The two-dimensional motion contrast enface image 71 is displayed on the right side of the display screen. On the lateral side of the two-dimensional motion contrast enface image 71, the luminance averaged image 72 at a position of the marker A-A' displayed on the two-dimensional motion contrast enface image 71 is displayed. The luminance averaged image is generated based on the three-dimensional luminance tomographic information in the cut surface specified in the two-dimensional motion contrast enface image. The GUI 73 is displayed on the left side of the display screen. Further, in this case, for example, a display mode as indicated by the dotted line in FIG. 7 representing the detection result of the layer structure information may be superimposed on the luminance tomographic image shown in FIG. 7 or the polarization tomographic image, and the resultant may be displayed on the display portion 146.

The enface image refers to a two-dimensional image obtained by integrating, in a depth direction z, the three-dimensional pixel data in a predetermined range of the object to be inspected in the depth direction z, and projecting the resultant on an x-y plane perpendicular to the depth direction z. An image obtained by integrating the luminance values in the respective pixels is referred to as an enface luminance image, and an image obtained by integrating the motion contrasts in the respective pixels is referred to as a motion contrast enface image. That is, the image generating portion 147 integrates the pixel data of the luminance tomographic image corresponding to the pixel in the extracted region at each XY position in the Z direction, and determines the luminance value of the pixel at each XY position. In this case, the luminance value of the pixel at each XY position is not limited to a value obtained by integration of the luminance of each pixel in the Z direction, and may be a value obtained by other processes, e.g., an average value or a median value.

The configuration of the GUI 73 includes, from the right side, the name of each layer of the retina to be used for two-dimensional motion contrast image display, a check box for selecting each layer, and a slider for adjusting the threshold value for determining each display pixel with respect to the selected layer. When the inspector drags this slider with a mouse, the signal processing portion 144 receives this instruction to determine that process of changing the display threshold value is performed in Step S356 of FIG. 5. Along with the change of the display threshold value, the flow returns to Step S354, and the two-dimensional motion contrast enface image to be displayed is updated. That is, as represented in the GUI 73, in this embodiment, the threshold value is set for each detected layer.

When it is determined that no instruction to change the display threshold value is output in Step S356, the flow proceeds to Step S357, and it is determined whether or not an instruction to change the depth range for display is output. In this embodiment, in Step S357, it is determined whether or not the inspector has changed a check of a check box associated with the luminance averaged image 72 in order to change the selection of the layer (corresponding to the change in display range in the depth direction). When the check is changed, in Step S357, the display range of the motion contrast image enface image (equivalent to generation range of the enface image) is changed, and the flow returns to Step S354, to thereby update the two-dimensional motion contrast enface image to be displayed. In this embodiment, in the setting of the display range, an arbitrary layer can be selected using the detected layer, and the number of layers that can be selected can be limited.

It is desired that the border of each layer be displayed in superimposition on the luminance averaged image as a result of the segmentation, and marking be performed so that the selected layer can be easily recognized. Further, a Layer/Border radio button 74, which is present in the lowermost portion of the GUI 73, is a radio button for selecting a method of generating the two-dimensional motion contrast image. In this embodiment, when "Layer" is selected, the two-dimensional motion contrast image is generated based on the information of each pixel value of a three-dimensional motion contrast enface image of the entire region of the selected layer. When "Border" is selected, however, control is performed such that the selectable check boxes are limited to two adjacent check boxes. As a result, the two-dimensional motion contrast enface image is generated based on the information of each pixel value of a three-dimensional motion contrast image having a predetermined depth across a border of the selected two layers.

The display mode is not limited to the mode described herein, and the images obtained in this embodiment may be displayed in an arbitrary combination in accordance with the usage. Examples of the images obtained in this embodiment include the two-dimensional motion contrast enface image, the three-dimensional motion contrast image, the luminance averaged image, the polarization characteristic image, and the three-dimensional luminance image. FIG. 8B is an example in which, instead of the luminance averaged image 72, a polarization characteristic image (two-dimensional polarization tomographic image) 75 at a position of the marker B-B' in the two-dimensional motion contrast enface image 71 is displayed. In this case, there is displayed a polarization tomographic image generated based on the three-dimensional polarization tomographic information in a cut surface specified in the two-dimensional motion contrast enface image. Further, those images may be displayed in a superimposed manner.

Further, in the embodiment described above, the inspector changes the display threshold value and the depth range for display with reference to the display screen. This embodiment is not, however, limited thereto, and, for example, the layer or the region between the layer borders to be displayed may be determined in advance by an inspection set, and at a time point at which this inspection set is selected, the change instruction from the control portion 143 may be received. Further, also regarding the display threshold value, a threshold value determined in advance may be selected based on the specified layer or depth range to output an instruction.

Further, regarding the specified depth range for display, a specific region extracted as a display target is regarded as, for example, a region having a predetermined range in the depth direction of the cross section, which includes a certain inter-layer border in the cross section displayed as the luminance averaged image. Further, the specific region in this case can be regarded as, in the cross section, at least one of a region from a certain inter-layer border to a different inter-layer border, or a region extending in a predetermined first range in that is deeper and a predetermined second range that is shallower from the certain inter-layer border in the depth direction. Further, the specific region can also be regarded as, with a certain layer or a border between different layers being a reference, a predetermined region extending in a predetermined range in a direction deeper or shallower than a position separated by a predetermined distance in the depth direction with respect to the border being the reference.

As described above, according to this embodiment, using the result of performing the segmentation based on the luminance information and the polarization information, the motion contrast image can be generated and displayed more accurately. Further, even in an eye to be inspected that has a disease resulting in, for example, the deformed or altered RPE, each layer can be appropriately recognized, and a motion contrast image useful for diagnosis can be generated.

Second Embodiment

In the above-mentioned first embodiment, there is described a method of performing the segmentation using the position information of the RPE obtained by the DOPU image, which is one of the polarization information, to thereby generate the two-dimensional motion contrast enface image by OCTA. In contrast, in a second embodiment of the present invention, there is described an example of using a retardation image referring to the retardation, which is one of the polarization parameters described above. The configuration, or the like, of the apparatus in this embodiment is similar to that in the first embodiment, and hence description thereof is omitted herein. In the following, part of polarization image generation different from that in the first embodiment is only described.

Retardation Image Generation

In this embodiment, the image generating portion 147 generates a retardation image from the luminance image having polarization components that are orthogonal to each other. A value $\delta$ of each pixel of the retardation image is obtained by quantifying the phase difference between the above-mentioned H polarization component and V polarization component at the position of each pixel forming the luminance image, and is calculated by Expression 4 based on the tomographic signals $A_H$ and $A_V$.

$$\delta = \arctan\left[\frac{A_V}{A_H}\right]. \qquad \text{Expression 4}$$

The retardation image is generated based on the value δ obtained by Expression 4 so that a layer having a birefringent property as the retinal nerve fiber layer (RNFL) can be recognized. In this embodiment, the signal processing portion 144 detects the RNFL from the retardation image (three-dimensional polarization tomographic information) obtained with respect to the plurality of B-scan images.

Retardation Map Generation

The signal processing portion 144 generates a retardation map, which is one example of polarization planar images (polarization Enface images), from the retardation image obtained with respect to the plurality of B-scan images. When the retardation map is to be generated, first, the signal processing portion 144 detects the retinal pigment epithelium (RPE) in each B-scan image. The RPE has a depolarization property. Therefore, the distribution of the retardation is examined in each A-scan in a range not including the RPE from an inner limiting membrane (ILM) along the depth direction, and the maximum value in the distribution is set as a representative value of the retardation in the A-scan. The map generating portion 148 generates the retardation map by performing the above-mentioned process on all of the retardation images.

Birefringence Map Generation

The image generating portion 147 performs linear approximation of the value δ of the retardation in a range from the ILM to the retinal nerve fiber layer (RNFL) in each A-scan image of the retardation image generated earlier, and determines its slope as a birefringence at a position on the retina of the corresponding A-scan image. This process is performed on all of the acquired retardation images, to thereby generate the birefringence map representing the birefringence as an example of the polarization planar image (polarization Enface image). Then, the map generating portion 148 uses the birefringence value to perform the segmentation of the RNFL.

Process Operation

Next, a procedure of a specific process of the image forming method of this embodiment is described. The basic process flow of this embodiment is the same as the process operation of the first embodiment, and, hence, a schematic description thereof is omitted. A detailed process of Step S253 and Step S254 in the process flow illustrated in FIG. 4 is different. Therefore, the process in this embodiment corresponding to those steps is described below as Step S253A and Step S254A, respectively.

In this embodiment, in Step S253A, the image generating portion 147 generates a retardation image. In Step S254A, the image generating portion 147 performs a process of generating the retardation image to obtain the position of the RNFL. In the retardation image, the RNFL can be accurately detected due to the polarization characteristic of the eye to be inspected. In this embodiment, segmentation adjustment performed in Step S340 of FIG. 3 is performed based on the detected RNFL position information. The first threshold processing in Step S360 is performed based on the luminance averaged image subjected to the segmentation process using this RNFL position information.

In the process described above, the method of performing segmentation based on the RNFL position information obtained by the polarization-sensitive OCT, and combining the result with the motion contrast information is described. The layer to be used in this embodiment is not, however, limited to the RNFL, and this embodiment is applicable to other regions as long as the segmentation using the birefringence information is possible. For example, using the polarization characteristic of the vessel wall, the vessel may be specified, and the result may be combined with the motion contrast information. In this manner, the result of calculating the blood flow information, which is performed in Step S390 of FIG. 3, can be improved in reliability. Further, the value δ of the retardation with respect to an arbitrary nerve fiber obtained from an arbitrary A-scan image is changed continuously with the value δ of the retardation of the nerve fiber obtained from the A-scan image in the vicinity. Therefore, the change in value of the retardation is reduced as compared to that of other layers, and, hence, segmentation may be performed using this fact. In this case, the nerve fiber is recognized as a layer exhibiting directionality in the three-dimensional polarization tomographic information, e.g., the orientation. Further, the image generating portion 147 can also generate a polarization planar image (polarization Enface image) using the orientation or the DOPU.

Third Embodiment

In the embodiments described above, OCTA calculated using the luminance information and the polarization information of the optical coherence tomography as region structure information is described. Now, an example will be described in which the motion contrast is calculated using the interference signals of light beams having two polarization components, specifically, light having an H polarization component and light having a V polarization component, to thereby acquire an OCTA image. According to a third embodiment of the present invention, with an operation of acquiring the luminance image (tomographic signal) for one frame in the related art, double tomographic signals can be acquired from the signal of the light having the H polarization component and the light having the V polarization component. Therefore, the number m of repetition times can be reduced.

Apparatus Configuration

Configurations of the optical coherence tomographic signal generating portion 800 and the control portion 143 according to this embodiment are similar to those in the first embodiment, and, hence, a detailed description thereof is omitted herein.

Signal Process

In the above-mentioned first and second embodiments, one luminance image is calculated from light beams having respective polarization components, but in this embodiment, the signal processing portion 144 generates two luminance images, specifically, a luminance image corresponding to the light having the H polarization component and a luminance image corresponding to the light having the V polarization component.

Process Operation

Next, a procedure of a specific process of the image forming method of this embodiment is described. The basic process flow of this embodiment is the same as the process flow of the first embodiment, and, hence, a schematic description thereof is omitted. A detailed process of Step S240, Step S260, Step S300, and Step S350 in the process flow illustrated in FIG. 3 is different. Therefore, the process in this embodiment corresponding to those steps is described below in detail as Step S240B, Step S260B, Step S300B, and Step S350B, respectively.

In this embodiment, in Step S240B, the image generating portion 147 extracts two individual interference signals based on the light beams having the respective H and V polarization components from the respective tomographic signals $A_H$ and $A_V$. In the first embodiment, an expression of generating one intensity image by the polarization-sensitive OCT is represented by Expression 1. In this embodiment, however, two intensity images are generated from the respective interference signals obtained by the light beams having the respective H and V polarization components. Specifically, the tomographic signal $A_H$ obtained by the light having the H polarization component and the tomographic signal $A_V$ obtained by the light having the V polarization component are each subjected to an FFT process. With this, different luminance images can be generated based on the respective polarization components. Further, the image generating portion 147 simultaneously generates the above-mentioned polarization characteristic image.

In Step S260B, the image generating portion 147 determines whether or not the index j representing the number of repetition times reaches a predetermined number, specifically, m. In this embodiment, there are two luminance images obtained after the FFT process, and hence the number of repetition times may be m/2 when it is intended to obtain tomographic signals of m frames as in the first embodiment. Therefore, in Step S260B, when j is less than the number m/2 of repetition times, the flow returns to Step S240B to execute the process thereafter. When j is greater than the number m/2 of repetition times, the flow proceeds to next Step S270 and subsequent steps to proceed to Step S300B.

In Step S300B, the image generating portion 147 uses the luminance images obtained in Step S280 and the luminance averaged image obtained in Step S290, to thereby perform the above-mentioned luminance image segmentation. After that, in Step S340, the map generating portion 148 uses the luminance averaged image and the polarization characteristic image to perform the segmentation. The segmentation may be RPE segmentation using the DOPU image, or RNFL segmentation using the retardation image.

In Step S350B, the signal processing portion 144 calculates the motion contrast from the luminance images obtained based on the respective H and V polarization components. Subsequently, the first threshold processing of Step S360 is executed based on the three-dimensional motion contrast data obtained here and the result of the segmentation adjustment process of Step S340. Using the polarization-sensitive OCT apparatus described above, the three-dimensional blood flow image can be obtained with a half number m/2 of repetition times.

OTHER EMBODIMENTS

The present invention has been described in detail above, but the present invention is not limited to the above-mentioned embodiments, and may be carried out with various modifications and changes without departing from the spirit of the present invention. For example, in the embodiments described above, the case in which the object to be inspected is an eye is described, but the present invention is also applicable to an object to be inspected other than an eye, e.g., skin or an organ. In this case, the present invention includes an aspect as a medical device other than an ophthalmologic apparatus, e.g., an endoscope. Therefore, it is desired that the present invention be understood as an inspection apparatus exemplified by the ophthalmologic apparatus and that the eye to be inspected be understood as one aspect of the object to be inspected.

Embodiments of the present invention can also be realized by a computer of a system or an apparatus that reads out and executes computer executable instructions (e.g., one or more programs) recorded on a storage medium (that may also be referred to more fully as a 'non-transitory computer-readable storage medium') to perform the functions of one or more of the above-described embodiments and/or that includes one or more circuits (e.g., an application specific integrated circuit (ASIC)) for performing the functions of one or more of the above-described embodiments, and by a method performed by the computer of the system or the apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
    a tomographic signal obtaining unit configured to obtain tomographic signals of light beams, the light beams respectively having a different polarization from each other and being obtained by splitting combined light obtained by combining return light and reference light, the return light being from an object to be inspected that is irradiated with measuring light;
    an information obtaining unit configured to obtain (i) three-dimensional polarization tomographic information, and (ii) three-dimensional motion contrast information of the object to be inspected, by commonly using at least one of the obtained tomographic signals;
    an extracting unit configured to extract a specific region of the object to be inspected using the obtained three-dimensional polarization tomographic information; and
    an image generating unit configured to generate a motion contrast enface image of the extracted specific region using the obtained three-dimensional motion contrast information.

2. The image processing apparatus according to claim 1, further comprising a display control unit configured to cause a display unit to display the generated motion contrast enface image with at least one of (i) a two-dimensional luminance tomographic image of the object to be inspected, and (ii) a two-dimensional polarization tomographic image of the object to be inspected at a position specified in the generated motion contrast enface image.

3. The image processing apparatus according to claim 2, wherein the image generating unit is configured to generate a polarization enface image in the extracted specific region using the three-dimensional polarization tomographic information, and wherein the display control unit is configured to cause the display unit to display a display mode for selecting the generated motion contrast enface image and the generated polarization enface image, to thereby display the selected images on the display unit.

4. The image processing apparatus according to claim 3, wherein the display control unit is configured to cause the display unit to display a display mode for specifying the extracted specific region.

5. The image processing apparatus according to claim 1, wherein the extracting unit is configured to extract a specific layer using the three-dimensional polarization tomographic information, to thereby extract the specific region using the extracted specific layer.

6. The image processing apparatus according to claim 5, wherein the information obtaining unit is configured to obtain three-dimensional luminance tomographic information of the object to be inspected by commonly using at least one of the tomographic signals, and wherein the extracting unit is configured to extract the specific layer using the three-dimensional luminance tomographic information, and to extract the specific region using a result of position alignment between the specific layer extracted using the three-dimensional polarization tomographic information and the specific layer extracted using the three-dimensional luminance tomographic information.

7. The image processing apparatus according to claim 5, wherein the image generating unit is configured to use motion contrast data of the extracted specific layer to determine a threshold value for performing a threshold processing on the motion contrast data in the specific region.

8. The image processing apparatus according to claim 5, wherein the object to be inspected comprises a retina of an eye, and wherein the specific layer comprises a layer that depolarizes the light beams having the different polarizations.

9. The image processing apparatus according to claim 5, wherein the object to be inspected comprises a retina of an eye, and wherein the specific layer comprises a layer exhibiting directionality in the three-dimensional polarization tomographic information.

10. The image processing apparatus according to claim 1, wherein the three-dimensional polarization tomographic information comprises information of at least one of retardation, birefringence, degree of polarization uniformity (DOPU), and orientation, which is generated using the tomographic signals obtained using the light beams having the different polarizations of a vertical polarization and a horizontal polarization.

11. The image processing apparatus according to claim 1, wherein the three-dimensional motion contrast information is obtained using a signal representing time modulation between corresponding pixels among a plurality of tomographic signals obtained by scanning the measuring light that is scanned with an intention to acquire tomographic signals of the same cross section in the object to be inspected.

12. The image processing apparatus according to claim 1, wherein the three-dimensional motion contrast information is obtained using a signal representing time modulation between pixels corresponding to a plurality of tomographic signals normalized based on the light beams having the different polarizations.

13. An image processing apparatus comprising:
a tomographic signal obtaining unit configured to obtain tomographic signals of light beams, the light beams respectively having a different polarization from each other and being obtained by splitting combined light obtained by combining return light and reference light, the return light being from an object to be inspected that is irradiated with measuring light;
an information obtaining unit configured to obtain (i) three-dimensional polarization tomographic information, and (ii) three-dimensional tomographic intensity information of the object to be inspected, by commonly using at least one of the obtained tomographic signals;
an extracting unit configured to extract a specific region of an object to be inspected using the obtained three-dimensional polarization tomographic information; and
an image generating unit configured to generate an enface image of the extracted specific region using the obtained three-dimensional tomographic intensity information.

14. The image processing apparatus according to claim 1, wherein the specific region comprises a region in a predetermined range in a depth direction of a cross section of the object to be inspected, which includes a certain inter-layer border in the cross section.

15. The image processing apparatus according to claim 14, wherein the specific region comprises, in the cross section, at least one of (i) a region from the certain inter-layer border to a different inter-layer border, and (ii) a region extending in a predetermined first range in a that is deeper and a predetermined second range that is shallower from the certain inter-layer border in the depth direction.

16. The image processing apparatus according to claim 1, wherein the tomographic signal obtaining unit is an optical coherence tomographic signal generating portion.

17. An image processing method comprising:
obtaining tomographic signals of light beams, the light beams respectively having a different polarization from each other and being obtained by splitting combined light obtained by combining return light and reference light, the return light being from an object to be inspected that is irradiated with measuring light;
obtaining (i) three-dimensional polarization tomographic information, and (ii) three-dimensional motion contrast information of the object to be inspected, by commonly using at least one of the obtained tomographic signals;
extracting a specific region of the object to be inspected using the obtained three-dimensional polarization tomographic information; and
generating a motion contrast enface image of the extracted specific region using the obtained three-dimensional motion contrast information.

18. An image processing method comprising:
obtaining tomographic signals of light beams, the light beams respectively having a different polarization from each other and being obtained by splitting combined light obtained by combining return light and reference light, the return light being from an object to be inspected that is irradiated with measuring light;
obtaining (i) three-dimensional polarization tomographic information, and (ii) three-dimensional tomographic intensity information of the object to be inspected, by commonly using at least one of the obtained tomographic signals;

extracting a specific region of an object to be inspected using the obtained three-dimensional polarization tomographic information; and generating an enface image of the extracted specific region using the obtained three-dimensional tomographic intensity information.

19. A non-transitory storage medium having stored thereon a program for causing a computer to execute the respective steps of the image processing method according to claim 17.

20. A non-transitory storage medium having stored thereon a program for causing a computer to execute the respective steps of the image processing method according to claim 18.

21. The image processing apparatus according to claim 1, wherein the three-dimensional polarization tomographic information includes information relating to an optical characteristic of a tissue existing in the specific region, the optical characteristic being provided in accordance with the light beams having polarizations different from each other.

22. The image processing apparatus according to claim 1, wherein the measuring light and the reference light are obtained from light from a light source, and a scanning operation with the measuring light is performed in three dimensions.

23. The image processing apparatus according to claim 1, wherein the combined light is split into light having a vertical polarization component and light having a horizontal component, and the tomographic signal obtaining unit outputs the tomographic signals of a light beam having the vertical polarization component and a light beam having a horizontal polarization component.

24. The image processing apparatus according to claim 13, wherein the three-dimensional polarization tomographic information includes information relating to an optical characteristic of a tissue existing in the specific region, the optical characteristic being provided in accordance with the light beams having polarizations different from each other.

25. The image processing apparatus according to claim 13, wherein the measuring light and the reference light are obtained from light from a light source, and a scanning operation with the measuring light is performed in three dimensions.

26. The image processing apparatus according to claim 13, wherein the combined light is split into light having a vertical polarization component and light having a horizontal component, and the tomographic signal obtaining unit outputs the tomographic signals of a light beam having the vertical polarization component and a light beam having a horizontal polarization component.

* * * * *